United States Patent
Kim et al.

(10) Patent No.: US 7,682,071 B2
(45) Date of Patent: Mar. 23, 2010

(54) MEASURING APPARATUS

(75) Inventors: Dong-Sik Kim, Pohang (KR); Sun-Rock Choi, Pohang (KR)

(73) Assignees: Postech Academy-Industry Foundation, Pohang (KR); Postech Foundation, Pohang (KR)

( * ) Notice: Subject to any disclaimer, the term of this patent is extended or adjusted under 35 U.S.C. 154(b) by 0 days.

(21) Appl. No.: 11/579,433

(22) PCT Filed: Oct. 30, 2006

(86) PCT No.: PCT/KR2006/004449

§ 371 (c)(1), (2), (4) Date: Nov. 3, 2006

(87) PCT Pub. No.: WO2007/052925

PCT Pub. Date: May 10, 2007

(65) Prior Publication Data

US 2008/0291967 A1    Nov. 27, 2008

(30) Foreign Application Priority Data

Oct. 31, 2006  (KR) ...................... 10-2005-0103246

(51) Int. Cl.
  *G01N 25/00* (2006.01)
  *G01K 7/00* (2006.01)
  *G01K 13/00* (2006.01)
(52) U.S. Cl. .......................... 374/43; 374/163; 374/147
(58) Field of Classification Search ................... 374/43, 374/163, 147
See application file for complete search history.

(56) References Cited

U.S. PATENT DOCUMENTS

| 4,621,929 A | * | 11/1986 | Phillips | 374/43 |
| 5,003,815 A | * | 4/1991 | Martin et al. | 73/105 |
| 5,499,313 A | * | 3/1996 | Kleinerman | 385/123 |
| 5,713,665 A | * | 2/1998 | Kato et al. | 374/43 |
| 5,929,438 A | * | 7/1999 | Suzuki et al. | 850/50 |
| 6,200,022 B1 | * | 3/2001 | Hammiche et al. | 374/46 |

(Continued)

FOREIGN PATENT DOCUMENTS

EP    1 422 518 A1    5/2004

(Continued)

OTHER PUBLICATIONS

Borca-Tasciuc et al., "Thermal Conductivity Measurement and Microscopy of Thin Film Structures," 16$^{th}$ *International Conference on Thermoelectrics*, pp. 726-729 (1997).

(Continued)

*Primary Examiner*—Gail Verbitsky
*Assistant Examiner*—Mirellys Jagan
(74) *Attorney, Agent, or Firm*—Marshall, Gerstein & Borun LLP (57) ABSTRACT

A measuring apparatus is provided. The measuring apparatus includes i) a point temperature sensor that has a tip and measures a temperature of an object, ii) a laser that heats the tip of the point temperature sensor by emitting a laser beam, iii) an optical member that is located between the laser and the point temperature sensor, iv) a measuring device that detects and measures a signal from the point temperature sensor, and v) a signal generator that supplies a reference signal.

9 Claims, 8 Drawing Sheets

U.S. PATENT DOCUMENTS

| | | | |
|---|---|---|---|
| 6,273,603 B1 * | 8/2001 | Cheindline et al. | 374/43 |
| 6,389,886 B2 * | 5/2002 | Daniels et al. | 73/105 |
| 6,405,137 B1 * | 6/2002 | Reading | 702/22 |
| 6,487,515 B1 * | 11/2002 | Ghoshal | 702/136 |
| 2002/0131476 A1 | 9/2002 | Baba et al. | 374/161 |
| 2003/0202556 A1 | 10/2003 | Taketoshi et al. | 374/45 |
| 2006/0062273 A1 | 3/2006 | Egolf et al. | |
| 2006/0067379 A1 * | 3/2006 | Djeu | 374/161 |
| 2008/0117951 A1 * | 5/2008 | Djeu | 374/159 |

FOREIGN PATENT DOCUMENTS

| | | |
|---|---|---|
| JP | 08-304315 | 11/1996 |
| KR | 2001-0064413 | 7/2001 |
| KR | 2001-305084 | 10/2001 |
| KR | 2002-0085091 | 11/2002 |
| WO | WO 2004/048953 | 6/2004 |

OTHER PUBLICATIONS

International Search Report for International Application No. PCT/KR2006/004449, dated Feb. 20, 2007.
Written Opinion for International Application No. PCT/KR2006/004449, dated Feb. 20, 2007.

* cited by examiner

MEASURING APPARATUS

TECHNICAL FIELD

The present invention relates to a measuring apparatus, and more particularly, to a measuring apparatus capable of measuring flux, pressure, velocity, and acceleration in addition to thermal properties.

BACKGROUND ART

Recently, as nano and bio technologies have been developed, it is important to measure thermal properties of a minute volume of a sample. In addition, since a material used for the nano and bio technologies is expensive, an amount of the material needed for measuring the thermal properties thereof is an important factor.

An ideal method of measuring thermal properties of an object having a minute volume employs point heating and point sensing techniques.

A conventional measuring apparatus that employs the point heating and point sensing techniques includes a Peltier vacuum gauge (see Korean Patent No. 0407815). The Peltier vacuum gauge measures a thermal conductivity coefficient of the periphery of a point temperature sensor using only one point temperature sensor and measures a degree of a vacuum from the thermal conductivity coefficient.

However, when the point heating is performed by using the Peltier effect, since heating and measuring techniques are based on the same theory such as a thermoelectric effect, heating and measuring circuits electrically interfere with each other. Accordingly, an additional circuit for distinguishing measured signals with respect to time is necessary.

In addition, it is impossible to measure the thermal properties in real time by extracting a temperature signal while heating a tip of the point temperature sensor by an alternating current source.

DISCLOSURE OF INVENTION

Technical Solution

Accordingly, the present invention provides a measuring apparatus with a good measuring sensitivity and an ultra small size that has a simple structure and measures a minute amount of a sample or a specific portion of an object.

The present invention also provides a measuring apparatus that measures flux, pressure, velocity, and acceleration in addition to thermal properties of the object.

Advantageous Effects

The present invention provides a measuring apparatus with a good measuring sensitivity and an ultra small size that has a simple structure and measures a minute amount of a sample or a specific portion of an object.

Accordingly, the measuring apparatus can measure thermal properties of the object by using a minute amount of a sample.

In addition, the measuring apparatus may employ a direct current source or an alternating current source. The measuring apparatus can perform real time measurement if necessary.

In addition, the measuring sensitivity of the measuring apparatus can be greatly improved.

In addition, the present invention also provides a measuring apparatus that can measure flux, velocity, and acceleration in addition to thermal properties of the object.

In addition, the measuring apparatus can measure the acceleration of the moving object while moving together with the moving object to which the measuring apparatus is fixed.

BEST MODE FOR CARRYING OUT THE INVENTION

According to an aspect of the present invention, there is provided a measuring apparatus including i) at least one point temperature sensor that has a tip and measures a temperature of an object, ii) a laser that heats the tip of the point temperature sensor by irradiating the tip of the point temperature sensor with a laser beam, iii) an optical member that is disposed between the laser and the point temperature sensor, iv) a measuring device that detects a signal from the point temperature sensor and measures the signal, and v) a signal generator that supplies a reference signal.

In the above aspect of the present invention, the optical member may include an optical lens.

In addition, the optical member may include an optical fiber.

In addition, the laser beam may be guided to the tip of the point temperature sensor through the optical fiber.

In addition, the object may be a fluid contained in a container, the tip of the point temperature sensor may be inserted into the object, and thermal properties of the object may be measured by heating the tip of the point temperature sensor by the laser beam emitted from the laser.

In addition, the object may be opaque fluid.

In addition, the container may have a transparent side.

In addition, the tip of the point temperature sensor may contact the transparent side of the container, and the side opposite to the side contacted by the tip of the point temperature sensor may be irradiated with the laser beam.

In addition, the object may be a solid, the tip of the point temperature sensor may contact a surface of a part of the object to be measured, and the thermal properties of the object may be measured by heating the tip of the point temperature sensor by the laser beam emitted from the laser.

In addition, the object may be a flowing fluid, the tip of the point temperature sensor may be inserted into the object, and flux of the object may be measured by heating the tip of the point temperature sensor by the laser beam emitted from the laser.

In addition, the at least one point temperature sensor may include a plurality of point temperature sensors.

In addition, the object may be an isolated fluid that moves together with the moving object, the tips of the plurality of point temperature sensors may be inserted into the object, the laser beam emitted from the laser may heat a tip among the tips of the point temperature sensors, and the acceleration of the moving object can be measured.

In addition, tips of the plurality of point temperature sensors may be sequentially arranged along a direction in which the acceleration of the moving object is to be measured.

In addition, the laser beam may heat a tip located at the center position among the tips of the plurality of the point temperature sensors.

In addition, the number of the point temperature sensors may be three.

In addition, the measuring apparatus may further include a heat sink having a tip.

In addition, the object may be an isolated fluid that moves together with the moving object. The tips of the plurality of point temperature sensors and the heat sink may be inserted into the object. The laser beam emitted from the laser may heat the tip of the heat sink, and the acceleration of the moving object may be measured.

In addition, the tips of the plurality of point temperature sensors and the tip of the heat sink may be sequentially arranged along the direction in which the acceleration of the moving object is to be measured, and the tip of the heat sink may be located at the center position of the tips of the point temperature sensors.

In addition, the measuring apparatus may further include a signal amplifier that amplifies a signal detected by the point temperature sensor.

In addition, the measuring apparatus may further include an optical modulator that modulates the laser beam emitted from the laser.

In addition, an alternating current (AC) source or a direct current (DC) source may be used.

A measuring apparatus according to an exemplary embodiment of the present invention will be described in detail hereinafter with reference to the accompanying drawings. As those skilled in the art would realize, the described embodiments may be modified in various different ways, all without departing from the spirit or scope of the present invention.

In addition, like reference numerals refers to like elements throughout the specification. The elements are representatively described in a first embodiment of the present invention. In a second embodiment, a detailed description of the elements in a second embodiment that are the same as those of the first embodiment of the present invention will be omitted.

To clearly describe an embodiment of the present invention, parts not related to the description are omitted. Like reference numerals refers to like elements throughout the specification.

Figure 1:
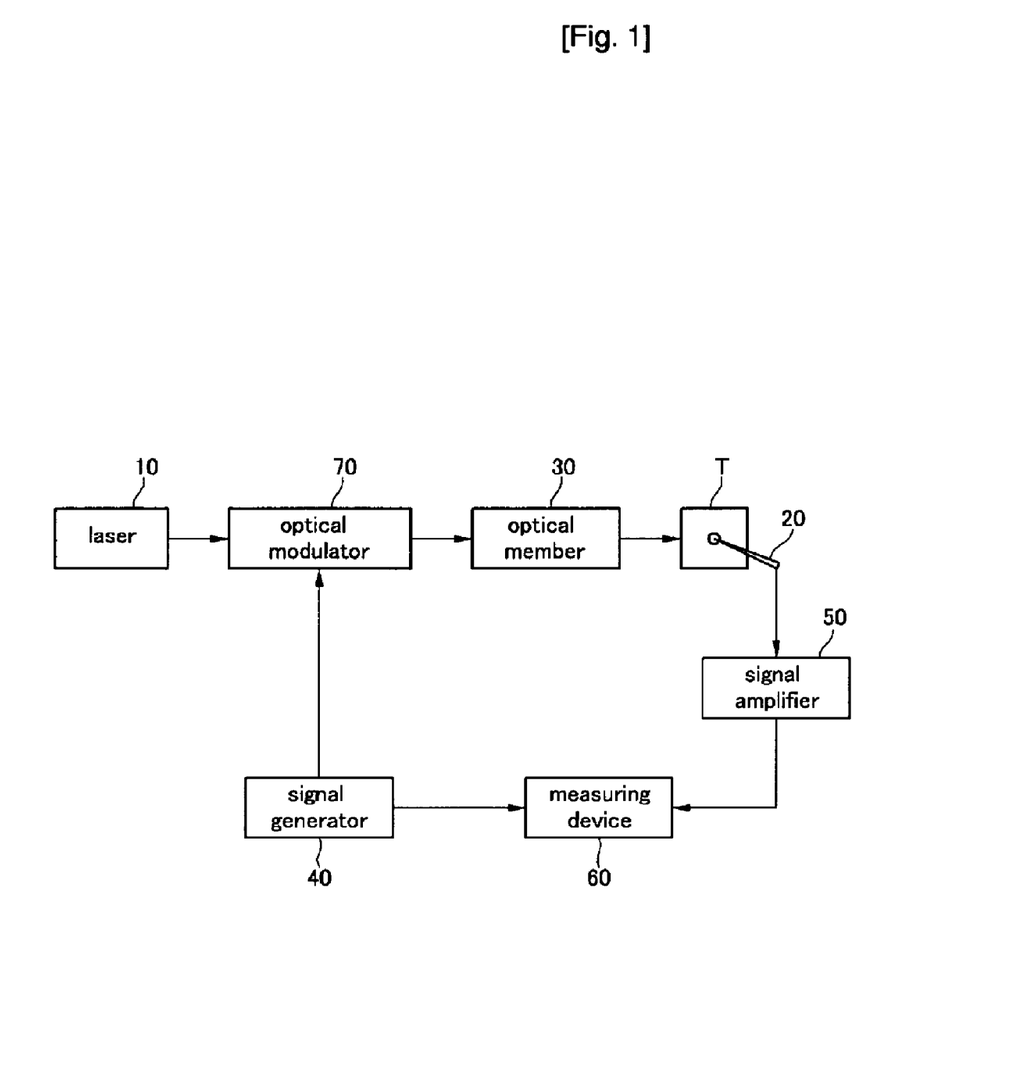
FIG. 1 is a block diagram illustrating a measuring apparatus according to a first embodiment of the present invention.

FIG. 1 illustrates a measuring apparatus according to a first embodiment of the present invention.

As shown in FIG. 1, the measuring apparatus includes a point temperature sensor 20, a laser 10, an optical member 30, a measuring device 60, and a signal generator 40. The measuring apparatus may further include an optical modulator 70 and a signal amplifier 50. An object T to be measured by the measuring device may be a part of a fluid or a solid having a minute volume.

The point temperature sensor 20 includes different kinds of metal wires. The junction obtained by bonding the different metal wires is the tip of the point temperature sensor. The point temperature sensor 20 measures the temperature change by inserting the tip of the point temperature sensor 20 into the object T or by contacting the tip thereof to the surface of the object T.

The laser 10 heats the tip of the point temperature sensor 20 by irradiating the tip with a laser beam. The optical member 30 focuses the laser beam emitted from the laser 10 onto a minute part. In addition, the optical modulator 70 modulates the laser beam emitted from the laser 10 so that the modulated laser beam has desirable characteristics. The laser beam emitted from the laser 10 is modulated by passing through the optical modulator 70 and is focused on the tip of the point temperature sensor 20 by passing through the optical member 30.

The optical modulator 70 may be an acousto-optic modulator (AOM) and an optical chopper.

The temperature of the tip of the point temperature sensor 20 can be calculated by Math FIG. 1 as follows:

$$T = \frac{q}{4\pi a k}\left\{\frac{1+ac_1}{c_1} - \frac{2a^2c_1^2c_2^2}{\pi}\right.$$

$$\left.\int_0^\infty \frac{e^{\alpha u^2 t/a^2}du}{[(u^2(1+ac_1)-ac_1c_2)]^2 + [u^3 - uac_1c_2]^2}\right\}$$

$$c_1 = h/k, \quad c_2 = \frac{4\pi a^3 \rho C}{M_s C_s}$$

MathFigure 1 where a is a size of the tip of the point temperature sensor 20, C is the specific heat of the object T, Cs is the specific heat of the tip of the point temperature sensor 20, c1 is the ratio between the thermal conductivities of the contact resistance and the object, c2 is the ratio between the heat capacities of the object T and the tip of the point temperature sensor 20, h is the contact resistance between the object T and the tip of the point temperature sensor, k is the thermal conductivity of the object T, Ms is the mass of the tip of the point temperature sensor 20, q is heat flux, t is time, u is an integration variable, α is thermal diffusivity of fluid, and π is the ratio of the circumference of a circle to its diameter.

When the heat flux is given by the laser 10, since the temperature of the tip of the point temperature sensor 20 is dependent upon the thermal conductivity of the object T, the thermal properties of the object T can be measured by using the temperature change of the tip of the point temperature sensor 20.

The measuring device 60 measures the temperature change with respect to time by detecting the signal from the point temperature sensor 20. Accordingly, the thermal properties of the object T can be obtained. The measuring device 60 may be an oscilloscope. The signal amplifier 50 amplifies the signal detected by the point temperature sensor 20 and transmits the amplified signal to the measuring device 60.

The signal generator 40 supplies a reference signal to the optical modulator 70 and the measuring device 60. The optical modulator 70 controls heating of the tip of the point temperature sensor 20 by adjusting the intensity of the laser beam emitted according to the reference signal from the signal generator 40. The measuring device 60 obtains information from the signal detected by the point temperature sensor 20 according to the reference signal of the signal generator 40.

Although the measuring apparatus of FIG. 1 includes the optical modulator 70, the present invention is not limited to the embodiment. When the measuring apparatus employs a laser diode (LD) as the laser 10, which independently modulates the waveform of the laser beam and emits the modulated laser beam, the optical modulator 70 may be omitted. In this case, the signal generator 40 supplies the reference signal directly to the laser 10.

As described above, the measuring apparatus employs the point heating and point sensing techniques by using the laser 10. Accordingly, the thermal properties of the object T can be measured by using a minute amount of a sample. In addition, the point temperature sensor 20 is heated by an optical method. The temperature of the object is measured through the thermoelectric effect. That is, since the heating process and the measuring process are separated from each other, a direct current source or an alternating current source may be used without limitation, and real time measurement can be performed during the heating process. In addition, since the laser 10 is independently driven with the point temperature sensor 20, the drive signal of the laser 10 and the signal detected by the point temperature sensor 20 do not interfere with each other. Therefore, the signal detected by the point temperature sensor 20 can be amplified to a desired extent. Accordingly, the measuring sensitivity of the measuring apparatus can be greatly improved.

Figure 2:
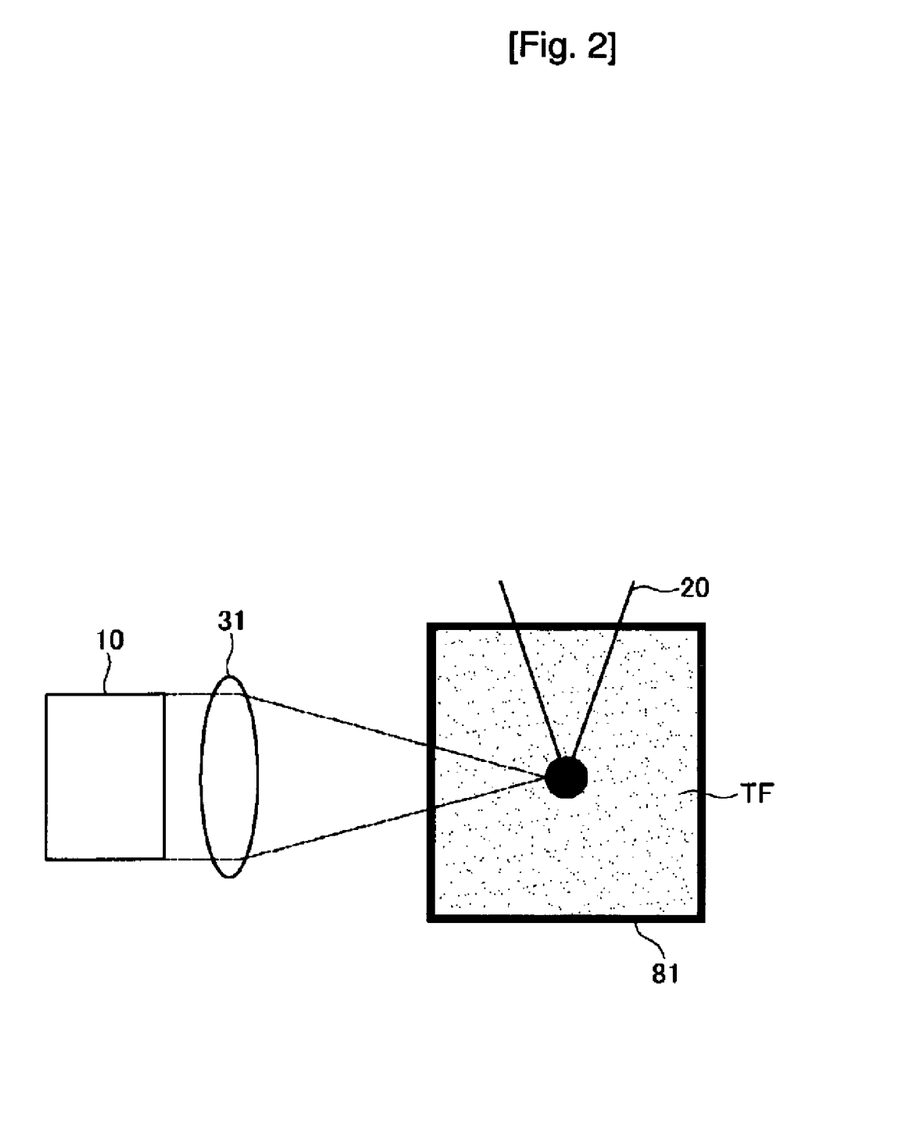
FIG. 2 is a schematic diagram illustrating main components of the measuring apparatus of FIG. 1.
Figure 3:
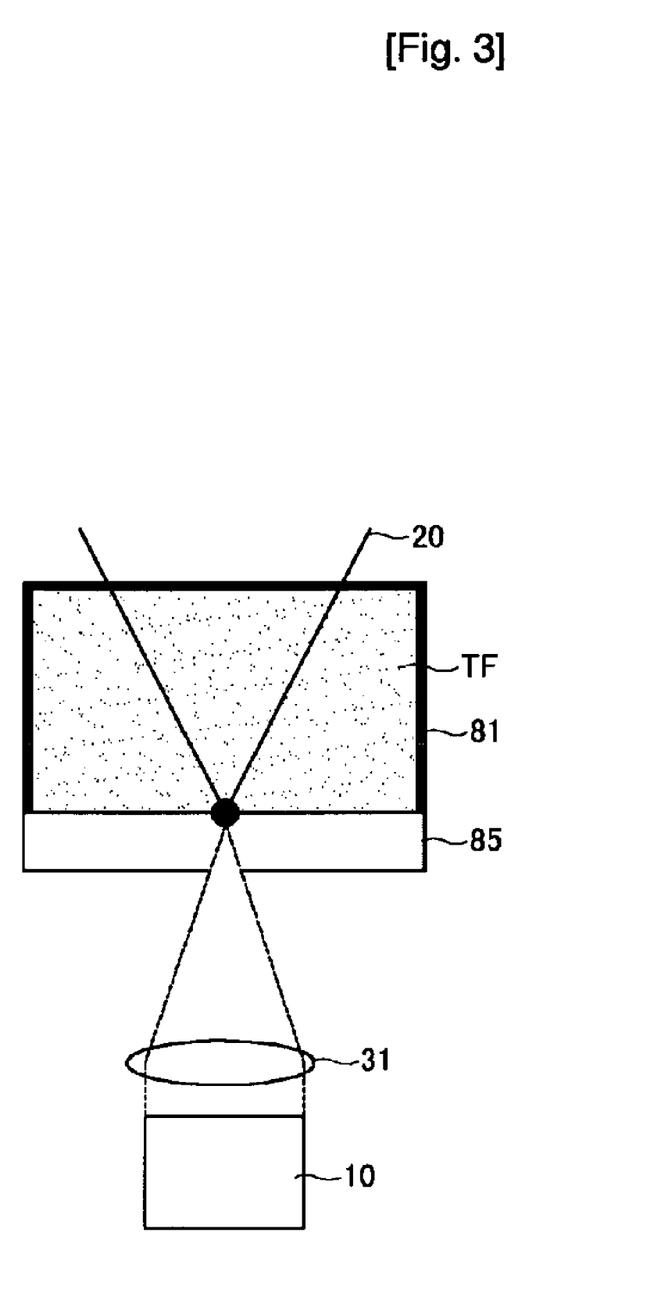
FIG. 3 is a schematic diagram illustrating another modified example of the measuring apparatus of FIG. 1.
Figure 4:
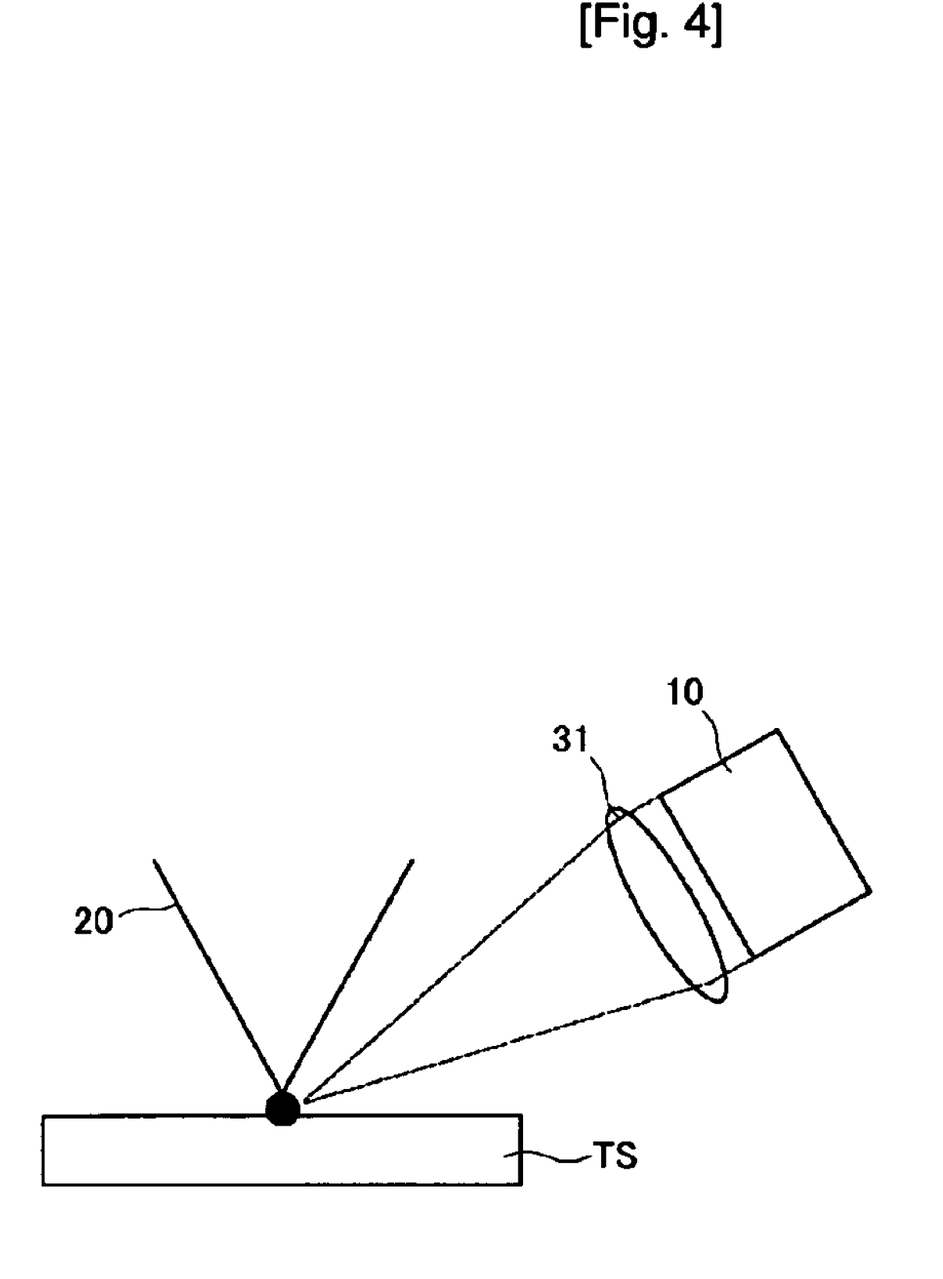
FIG. 4 is a schematic diagram illustrating another modified example of the measuring apparatus of FIG. 1.

Referring to FIGS. 2 to 4, a method of measuring the thermal properties of the object using the measuring apparatus according to the first embodiment of the present invention is described in detail. When the object to be measured is a fluid, TF is used as a reference symbol of the object. When the object to be measured is a solid, TS is used as a reference symbol of the object. As illustrated in FIGS. 2 to 4, according to the first embodiment of the present invention, an optical lens 31 is used as the optical member.

FIG. 2 illustrates a measuring method when the object TF to be measured is a transparent fluid.

As illustrated in FIG. 2, when the object TF to be measured is a transparent fluid, the object is contained in a container 81 and measured. The tip of the point temperature sensor 20 is inserted into the object TF, and the laser beam emitted from the laser 10 irradiates and heats the tip of the point temperature sensor 20. At this time, the thermal properties of the object TF are measured by measuring the temperature change of the tip of the point temperature sensor 20.

As described above, the thermal properties of the fluid having a minute volume can be effectively measured by the point heating and point sensing techniques using the laser 10.

FIG. 3 illustrates a measuring method when the object TF to be measured is an opaque fluid.

As illustrated in FIG. 3, when the object TF to be measured is an opaque fluid, the object is contained in a container 81 having a transparent side 85 and measured. The tip of the point temperature sensor 20 is heated by contacting the tip of the point temperature sensor 20 to the transparent side 85 of the container 81 and irradiating the side opposite to the side that the tip of the point temperature sensor 20 contacts with the laser beam. The thermal properties of the object TF are measured by measuring the temperature change of the tip of the point temperature sensor 20.

Since the opaque fluid absorbs the laser beam, when the thermal properties of the object are measured as illustrated in FIG. 2, it is difficult to accurately measure the thermal properties of the object. Therefore, as illustrated in FIG. 3, the container 81 has the transparent side 85 in order to transmit the laser beam. The thermal properties of the object TF are accurately measured by contacting the tip of the point temperature sensor 20 to the transparent side 85 and heating the tip using the laser beam.

As described above, the thermal properties of the opaque fluid having a minute volume can be effectively measured by the point heating and point sensing techniques using the laser 10.

FIG. 4 illustrates a measuring method when the object TS to be measured is a solid.

As illustrated in FIG. 4, the tip of the point temperature sensor 20 contacts a minute part of the solid object TS to be measured. The laser beam emitted from the laser 10 heats the tip of the point temperature sensor 20. The thermal properties of the object TS are measured by measuring the temperature change of the tip of the point temperature sensor 20.

As described above, the measuring apparatus can measure the thermal property distribution on the solid surface with a spatial accuracy that is about the tip size of the point temperature sensor 20. Accordingly, the measuring apparatus may be used as a thermal imaging microscope.

Figure 5:
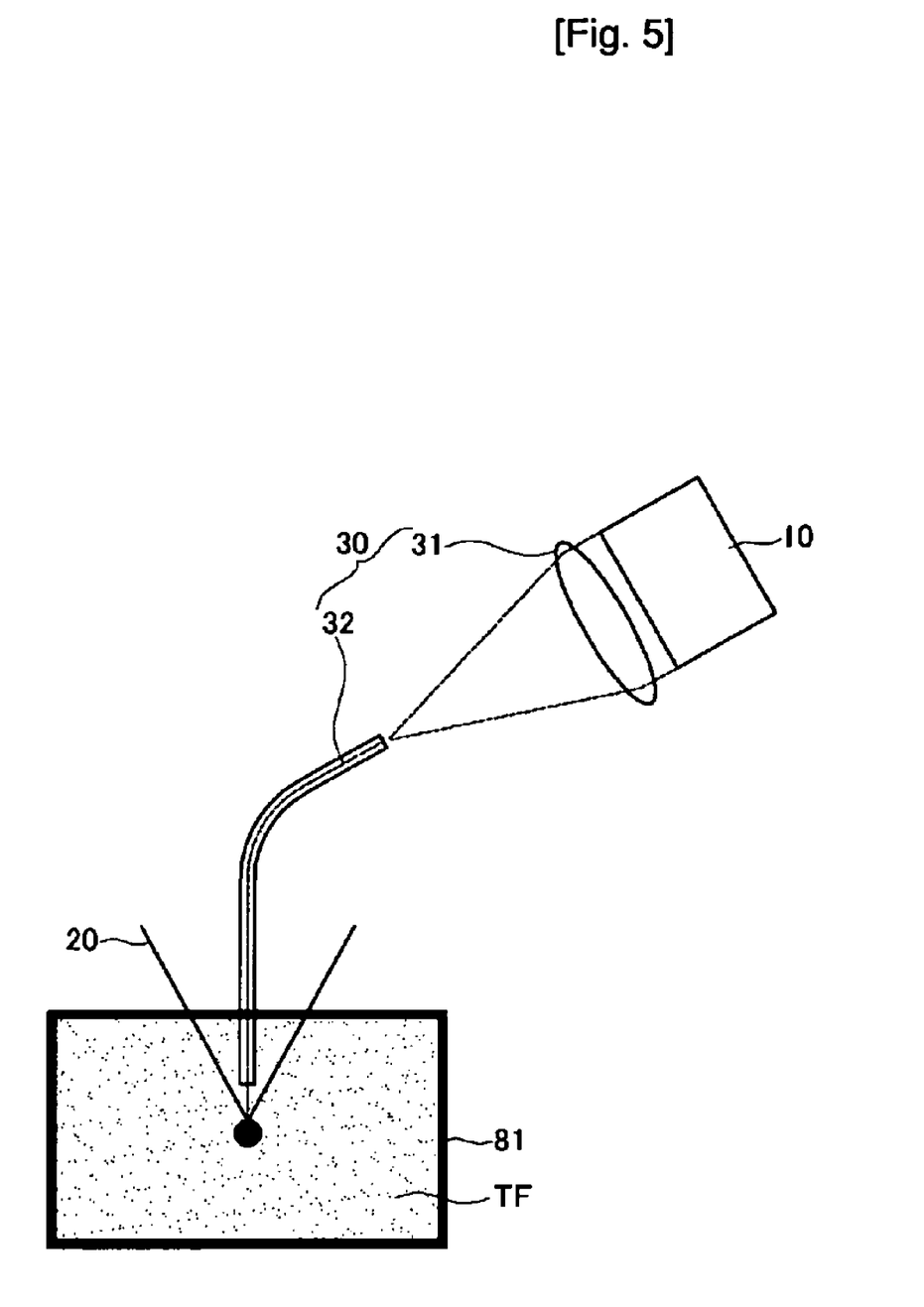
FIG. 5 is a schematic diagram illustrating main components of a measuring apparatus according to a second embodiment of the present invention.
Figure 6:
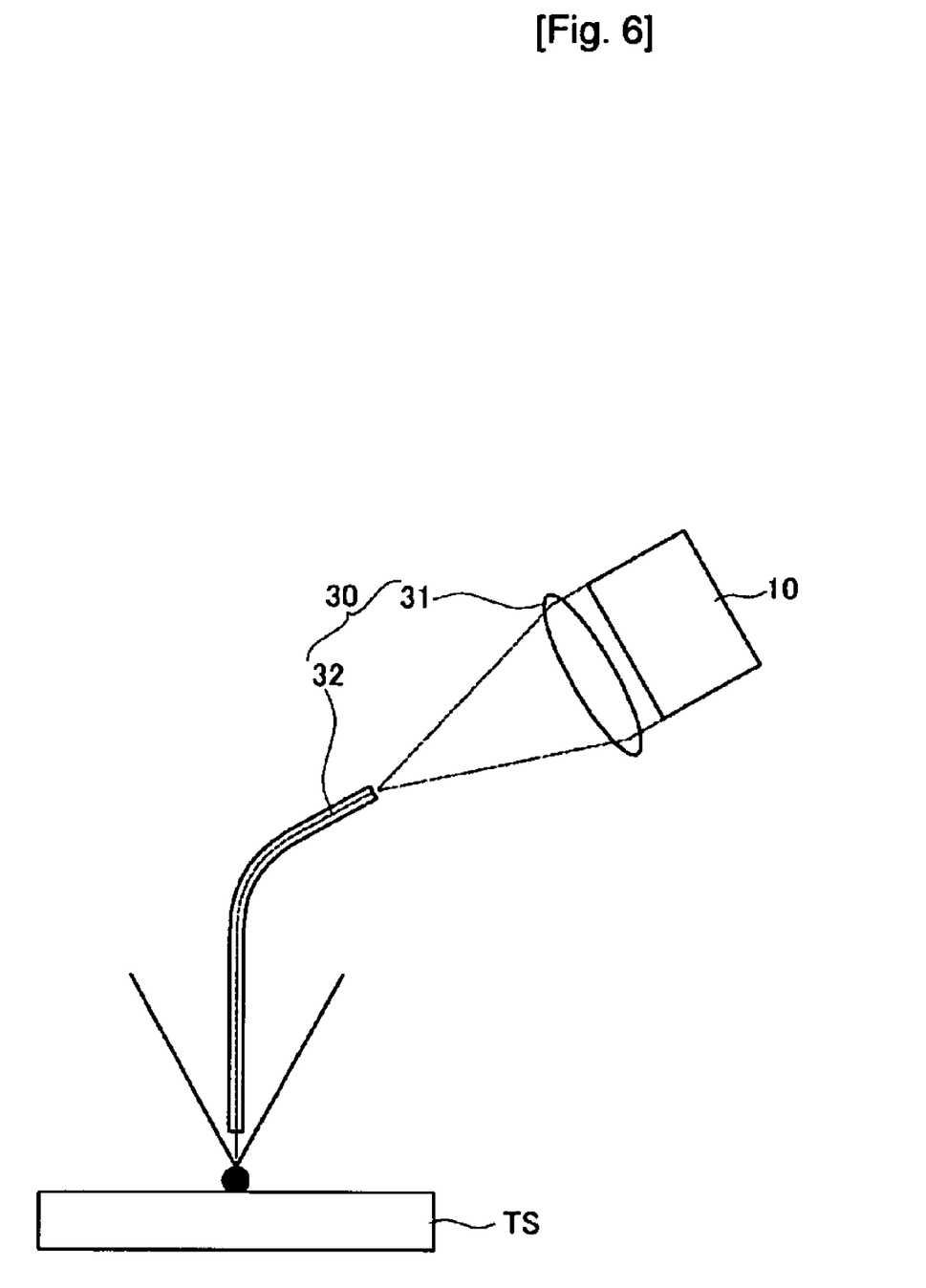
FIG. 6 is a schematic diagram illustrating another modified example of the measuring apparatus of FIG. 5.

Referring to FIGS. 5 and 6, a method of measuring the thermal properties of the object using the measuring apparatus according to the second embodiment of the present invention is described in detail. As illustrated in FIGS. 5 and 6, the optical member 30 according to the second embodiment of the present invention includes the optical lens 31 and an optical fiber 32. However, the present invention is not limited to the embodiment, and the optical lens 31 may be omitted. That is, the laser beam emitted from the laser 10 may be transmitted directly to the optical fiber 32 without passing through the optical lens 31.

FIG. 5 illustrates a measuring method when the object TF to be measured is a fluid.

As illustrated in FIG. 5, the fluid object TF to be measured is contained in the container 81, and the tip of the point temperature sensor 20 is inserted into the object TF contained in the container 81. One end of the optical fiber 32 is located near the tip of the point temperature sensor 20, and the other end of the optical fiber 32 is irradiated with the laser beam. The laser beam emitted from the laser 10 is guided by the optical fiber 32 to heat the tip of the point temperature sensor 20. At this time, the temperature change of the tip of the point temperature sensor 20 is measured, and the thermal properties of the object TF are measured.

The tip of the point temperature sensor 20 is accurately heated by the aforementioned structure. In addition, the thermal properties may be measured even in a region that the laser beam hardly irradiates. That is, a compact measuring apparatus with a simple structure and a high space accuracy using the optical fiber 32 can be achieved.

In addition, even when the object TF to be measured is an opaque fluid, the thermal properties can be effectively and accurately measured using the optical fiber 32. The optical fiber 32 helps the laser beam to accurately reach the tip of the point temperature sensor 20 without interference due to the opaque fluid. That is, since the laser beam reaches the tip of the point temperature sensor 20 after passing through the optical fiber 32, the laser beam is prevented from being absorbed or scattered due to the opaque fluid.

FIG. 6 illustrates a measuring method when the object TS to be measured is a solid.

As illustrated in FIG. 6, the tip of the point temperature sensor 20 contacts a minute part of the solid object TS to be measured. One end of the optical fiber 32 is located near the tip of the point temperature sensor 20. The other end of the optical fiber 32 is irradiated with the laser beam emitted from the laser 10. The laser beam emitted from the laser 10 is guided by the optical fiber to heat the tip of the point temperature sensor 20. The thermal properties of the object TS are measured by measuring the temperature change of the tip of the point temperature sensor 20.

The tip of the point temperature sensor 20 is accurately heated by the aforementioned structure. In addition, the thermal properties may be measured even in a region that the laser beam hardly irradiates. That is, a compact measuring apparatus with a simple structure and a high space accuracy using the optical fiber 32 can be achieved.

Figure 7:
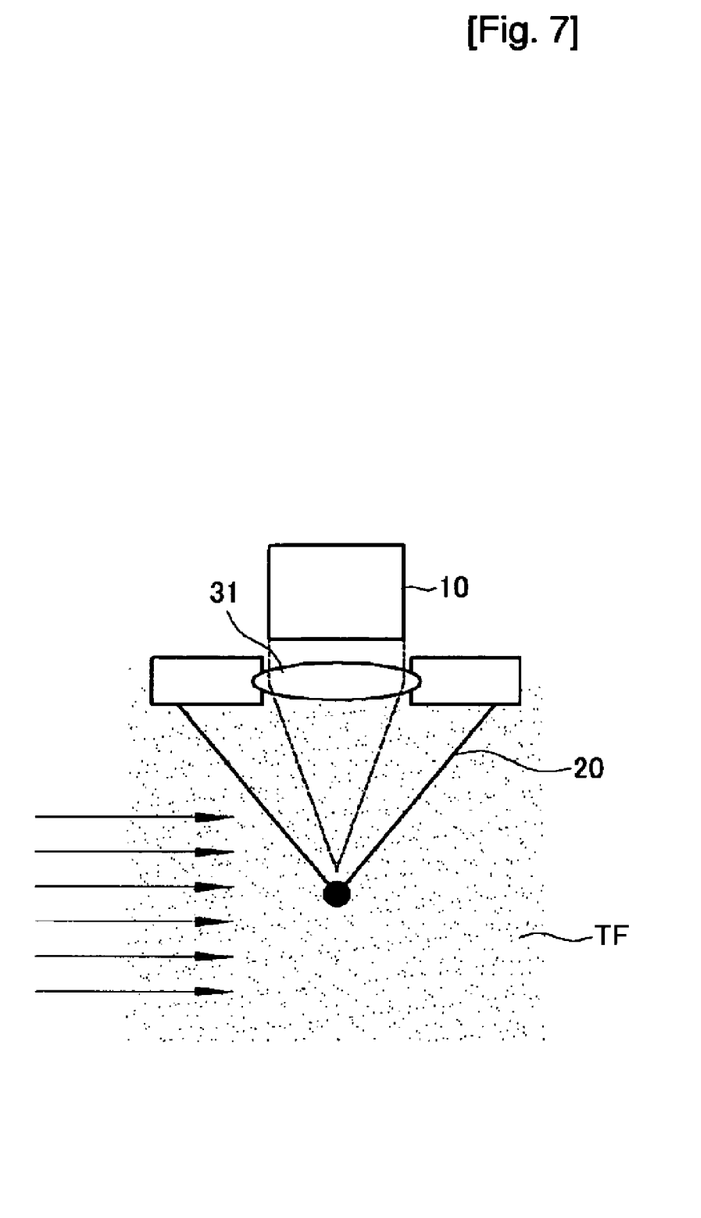
FIG. 7 is a schematic diagram illustrating main components of a measuring apparatus according to a third embodiment of the present invention.

Referring to FIG. 7, a method of measuring the flux of the fluid object TF using the measuring apparatus according to the third embodiment of the present invention is described in detail. As illustrated in FIG. 7, the object TF according to the third embodiment of the present invention is a flowing fluid. Although the optical lens 31 is used as the optical member 30 in FIG. 7, the present invention is not limited to the embodiment. Therefore, the optical fiber 32 (shown in FIG. 5) may be used as the optical member 30. Alternatively, the optical fiber 32 and the optical lens 31 may be used together as the optical member 30.

FIG. 7 illustrates a method for measuring flux of fluid when the object TF to be measured is a fluid.

As illustrated in FIG. 7, the tip of the point temperature sensor 20 is inserted into the flowing fluid, and the laser beam emitted from the laser 10 heats the tip of the point temperature sensor 20. The flux of the object TF is measured by measuring the temperature change of the tip of the point temperature sensor 20.

Since an amount of the heat that is applied to the tip of the point temperature sensor 20 and discharged to the fluid is a function of the velocity of the fluid, the flux and the velocity of the flowing fluid can be measured by using the amount of heat.

In addition, the velocity and the pressure in addition to the flux of the flowing fluid can be obtained by using the aforementioned method.

Figure 8:
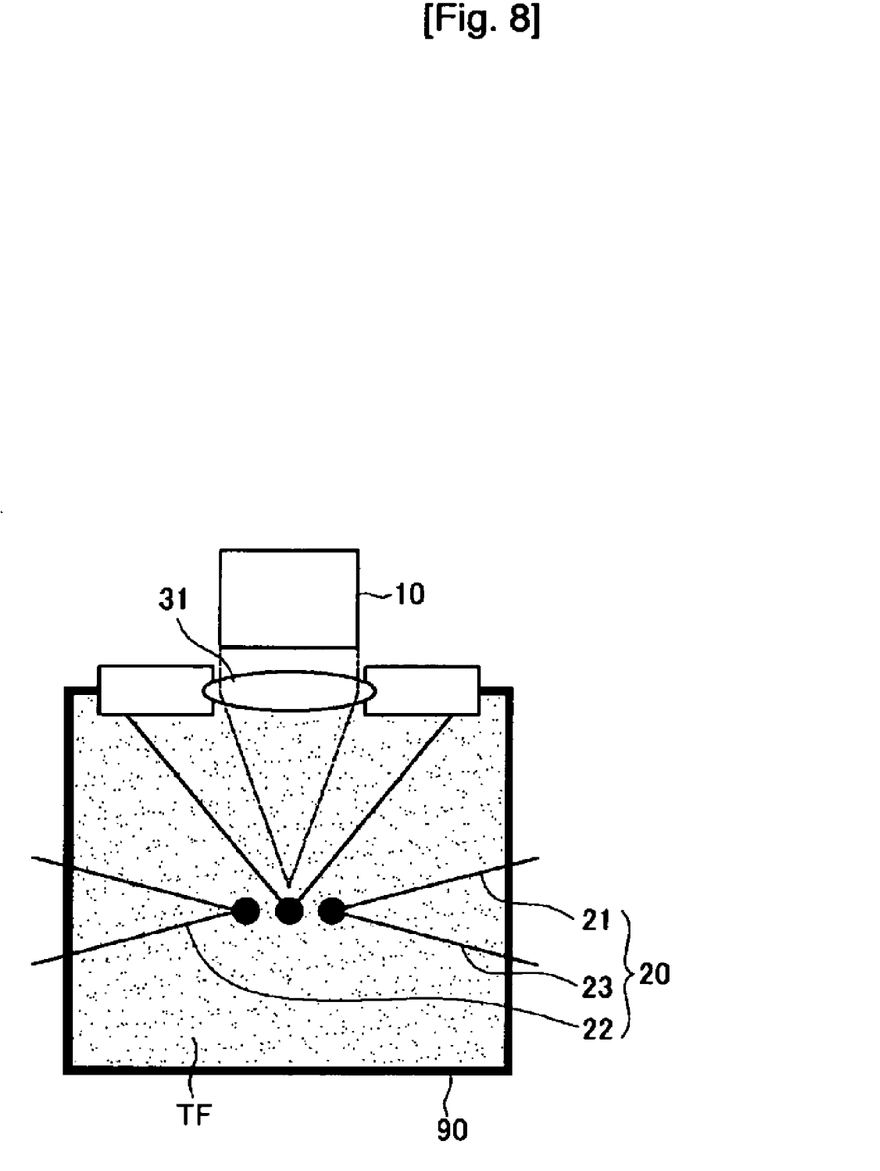
FIG. 8 is a schematic diagram illustrating main components of a measuring apparatus according to a fourth embodiment of the present invention.

Referring to FIG. 8, a method of measuring the acceleration of a moving object using the measuring apparatus according to the fourth embodiment of the present invention is described in detail. Specifically, the measuring apparatus can measure the acceleration of the object while moving together with the moving object to which the measuring apparatus is fixed. Although the optical lens 31 is used as the optical member 30 in FIG. 8, the present invention is not limited to the embodiment. Therefore, the optical fiber 32 (illustrated in FIG. 5) may be used as the optical member 30. Alternatively, the optical fiber 32 and the optical lens 31 may be used together as the optical member 30.

FIG. 8 illustrates a measuring apparatus for measuring acceleration of the moving object to which the measuring apparatus is fixed.

As illustrated in FIG. 8, the measuring apparatus includes the plurality of point temperature sensors 20 each of which has a tip, the laser 10 that emits the laser beam to the tips of the plurality of point temperature sensors 20, the optical lens 31 that focuses the emitted laser beam on the minute area, and a storage unit 90 that isolates and stores the fluid object TF.

The tips of the plurality of point temperature sensors 20 are inserted into the object TF. Then, the plurality of point temperature sensors 20 are sequentially arranged along the direction in which the acceleration of the moving object is to be measured. The laser 10 heats the tip located at a center position among the tips of the plurality of point temperature sensors 20.

The acceleration of the moving object is measured by measuring the temperature change of the tips of the point temperature sensors 22 and 23 near the heated tip of the point temperature sensor 21.

When the thermal properties of the moving object are changed due to the acceleration, the temperatures of the tips of the point temperature sensors 22 and 23 near the heated point temperature sensor 21 are changed. Since the change of the thermal properties is a function of the magnitude of the acceleration, the acceleration of the moving object can be measured by using the change.

In FIG. 8, a measuring apparatus having three point temperature sensors 20 is illustrated. As the number of the point temperature sensors 20 is increased, the measuring sensitivity is improved.

In addition, when the acceleration of the moving object is measured, the tip heated by the laser is not limited to the tip of the point temperature sensor 20. That is, the tip heated by the laser is a tip of a heat sink that can emit heat by absorbing the laser beam. Here, the heat sink has to include the tip that is similar to that of the point temperature sensor 20. Therefore, the laser 10 heats the tip of the heat sink, and the temperature change of the tip of the point temperature sensor 20 located near the tip of the heat sink is measured, thereby obtaining the acceleration of the moving object.

The measuring apparatus having the aforementioned structure can measure the thermal properties of the object by using a minute amount of a sample. In addition, the point temperature sensor 20 is heated by an optical method and the temperature of the object is measured through the thermoelectric effect. That is, since the heating process and the measuring process are separated from each other, the direct current source or an alternating current source may be available without limitation, and real time measurement can be performed during the heating process. In addition, since the laser 10 is independently driven with the point temperature sensor 20, the driving signal of the laser 10 and the signal detected by the point temperature sensor 20 do not interfere with each other. Therefore, the signal detected by the point temperature sensor 20 can be amplified to a desired extent. Accordingly, the measuring sensitivity of the measuring apparatus can be greatly improved.

In addition, since the thermoelectric characteristics of the fluid depends on the flux, the velocity, the acceleration, and the pressure of the fluid, the flux, the velocity, the acceleration, and the pressure of the fluid can be measured by using the measuring apparatus according to an embodiment of the present invention.

In addition, the measuring apparatus can measure the acceleration of the moving object while moving together with the moving object to which the measuring apparatus is fixed.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. A measuring apparatus comprising:
   at least one point temperature sensor that has a tip and measures a temperature of an object;
   a laser that heats the tip of the point temperature sensor by emitting a laser beam;

an optical member that is located between the laser and the point temperature sensor;

a measuring device that detects and measures a signal from the point temperature sensor;

a signal generator that is connected with the measuring device, the signal generator supplying a reference signal to the measuring device; and a container for containing the object, the container having a transparent side, wherein the tip of the point temperature sensor contacts the transparent side of the container, wherein a side opposite to the side that is contacted by the tip of the point temperature sensor is irradiated with the laser beam, and, wherein thermal properties of the object are measured by heating the tip of the point temperature sensor by the laser beam emitted from the laser.

2. The measuring apparatus of claim 1, wherein the optical member comprises an optical lens.

3. The measuring apparatus of claim 1, wherein the object is a fluid contained in the container.

4. The measuring apparatus of claim 1, wherein the object is an opaque fluid.

5. The measuring apparatus of claim 1, further comprising a signal amplifier that amplifies a signal detected by the point temperature sensor.

6. The measuring apparatus of claim 1, further comprising an optical modulator that modulates the laser beam emitted from the laser.

7. The measuring apparatus of claim 1, wherein an alternating current source or a direct current source is used.

8. The measuring apparatus of claim 1, wherein the optical member comprises an optical fiber.

9. The measuring apparatus of claim 8, wherein the laser beam is guided to the tip of the point temperature sensor through the optical fiber.

* * * * *